United States Patent
Berka et al.

(10) Patent No.: US 8,628,462 B2
(45) Date of Patent: Jan. 14, 2014

(54) SYSTEMS AND METHODS FOR OPTIMIZATION OF SLEEP AND POST-SLEEP PERFORMANCE

(75) Inventors: Chris Berka, Carlsbad, CA (US);
Djordje Popovic, Carlsbad, CA (US);
Gene Davis, Carlsbad, CA (US);
Matthew A. Yanagi, Carlsbad, CA (US)

(73) Assignee: Advanced Brain Monitoring, Inc., Carlsbad, CA (US)

( * ) Notice: Subject to any disclaimer, the term of this patent is extended or adjusted under 35 U.S.C. 154(b) by 312 days.

(21) Appl. No.: 12/574,631

(22) Filed: Oct. 6, 2009

(65) Prior Publication Data
US 2010/0087701 A1  Apr. 8, 2010

Related U.S. Application Data

(60) Provisional application No. 61/103,512, filed on Oct. 7, 2008.

(51) Int. Cl.
*A61M 21/00* (2006.01)
(52) U.S. Cl.
USPC .............................................. 600/27; 600/26
(58) Field of Classification Search
USPC ...................................................... 600/27, 26
See application file for complete search history.

(56) References Cited

U.S. PATENT DOCUMENTS

| | | | | |
|---|---|---|---|---|
| 5,163,426 A | * | 11/1992 | Czeisler et al. | 607/88 |
| 5,507,716 A | * | 4/1996 | LaBerge et al. | 600/27 |
| 7,041,049 B1 | * | 5/2006 | Raniere | 600/26 |
| 8,069,852 B2 | * | 12/2011 | Burton et al. | 128/204.18 |
| 2002/0169384 A1 | * | 11/2002 | Kowallik et al. | 600/529 |
| 2004/0002742 A1 | * | 1/2004 | Florio | 607/19 |
| 2005/0085738 A1 | * | 4/2005 | Stahmann et al. | 600/529 |
| 2005/0143617 A1 | * | 6/2005 | Auphan | 600/26 |
| 2005/0283039 A1 | | 12/2005 | Cornel | |
| 2006/0106275 A1 | | 5/2006 | Raniere | |
| 2006/0241708 A1 | * | 10/2006 | Boute | 607/17 |
| 2007/0249952 A1 | | 10/2007 | Rubin et al. | |
| 2008/0234785 A1 | | 9/2008 | Nakayama et al. | |
| 2009/0207028 A1 | * | 8/2009 | Kubey et al. | 340/575 |

OTHER PUBLICATIONS

International Search Report and Written Opinion for PCT/US2009/059836 issued May 13, 2010, 11 pages.

\* cited by examiner

*Primary Examiner* — Christine Matthews
*Assistant Examiner* — Sunita Reddy
(74) *Attorney, Agent, or Firm* — Procopio, Cory, Hargreaves & Savitch LLP

(57) ABSTRACT

Systems and methods for optimizing the sleep and post-sleep performance of individuals regardless of their environment and time available for sleep are provided. The systems and methods take into account factors that determine the effects of a sleep episode on dexterity, cognitive functions and the subjective feeling of fatigue after sleeping: duration and sleep architecture of the sleep episode, point on the circadian cycle at which the episode occurred, the amount of sleep debt accumulated prior to the episode and the subject's susceptibility to sleep deprivation. The systems and methods include monitoring of sleep architecture over a longer period of time, measurement of accumulated sleep debt and assessment and/or tailoring of the sleep architecture for each subsequent sleep episode, determining a desired sleep state in which the subject should be in, and generating sensory stimuli for guiding the subject to the desired sleep state.

26 Claims, 4 Drawing Sheets

SYSTEMS AND METHODS FOR OPTIMIZATION OF SLEEP AND POST-SLEEP PERFORMANCE

RELATED APPLICATION

This application claims the benefit of U.S. provisional patent application Ser. No. 61/103,512 entitled "An Apparatus and Method for Optimization of Sleep and Post-Sleep Performance," filed on Oct. 7, 2008, which is incorporated herein by reference in its entirety.

GOVERNMENT LICENSE RIGHTS

This invention was made with government support under Contract No. W3194Q-09-C- 0281, awarded by the Defense Advanced Research Projects Agency (DARPA), the. Small Business Innovation Research (SBIR) program. The government has certain rights in the invention.

FIELD OF THE INVENTION

The present invention generally relates to the field of monitoring sleep architecture and more specifically to systems and methods for monitoring sleep architecture of a subject, determining a desired sleep state or sleep pattern based on a sleep record for the subject, and guiding the subject toward a desired sleep state through one or more sleep patterns.

BACKGROUND

On average, healthy adults sleep between six and nine hours per night. The exact amount of sleep required by a person may vary greatly due to a number of factors associated with the person, such as the age of the person, the level of physical activity of the person, the use of alcohol, drugs, and/or medications by the person, and the overall condition of health. Contemporary sleep science distinguishes five stages of sleep (including wakefulness as a pre-sleep stage): a rested wakeful stage, non-rapid eye movement (NREM) sleep stages 1, 2, and 3, and rapid eye movement (REM) sleep. The various stages of sleep may be identified using various techniques, such as monitoring brainwave patterns using an electroencephalogram (EEG) technique, monitoring eye movements using a electrooculogram (EOG) technique, monitoring the movements of the chin using electromyogram (EMG) techniques, and/or other techniques for monitoring the physiological characteristics of a subject.

Rested wakefulness is characterized by low amplitude alpha waves (8-12 Hz) present in an EEG of a subject whose brain waves are being monitored. Alpha waves are brain waves typically exhibited while a subject is in a wakeful and relaxed state with the subject's eyes being closed. The alpha waves typically decrease in amplitude while the subject's eyes are opened or the subject is in a drowsy or sleeping state. NREM stage 1 is characterized by irregular theta waves of low amplitude present the EEG of a subject being monitored and slow rolling eye movements in present an EOG of the subject. NREM stage 2 is characterized by high frequency (12-16 Hz) bursts of brain activity called sleep spindles riding on top of slower brain waves of higher amplitude. During the NREM 2 stage, a gradual decline in heart rate, respiration and core body temperature occurs as the body prepares to enter deep sleep. NREM stage 3 is characterized by delta waves (1-3 Hz) of large amplitude that dominate for more than 20% of the time. Rapid eye movement (REM) sleep presents with a marked drop in muscle tone, and bursts of rapid eye movements that can be seen in the EOG. The EEG in REM is not specific and resembles that of wakefulness or NREM stage 1 sleep. Other physiological signals (breathing, heart rate) during REM sleep also exhibit a pattern similar to that occurring in an awakened individual.

Sleep stages come in cycles that repeat on average four to six times a night, with each cycle lasting approximately ninety to one hundred and twenty minutes. FIG. 1 illustrates a typical sleep cycle that includes an NREM stage 1, followed by an NREM stage 2, followed by an NREM stage 3, which is followed by a REM stage. The order of the stages of a sleep cycle can vary and the length of the sleep stages may also vary from person to person and from different sleep cycles can vary from sleep cycle to sleep cycle for a person. For example, NREM stage 3 may be more prevalent during sleep cycles that occur early in the night, while NREM stage 2 and REM sleep stages may be more prevalent in sleep cycles that occur later in the night. The sequence of sleep stages (NREM sleep stages 1, 2, 3 or the REM sleep stage) during an (overnight) sleep or (daytime) nap, sometimes interrupted with brief periods of wakefulness, is referred to as sleep architecture.

For optimal results from sleep, a balance between sleep stages is typically required over longer periods of time, such as days or weeks. Sleep deprivation, the persistent lack of a particular sleep stage (usually REM or NREM stage 3) over a period of even a few days can result in the deterioration of cognitive performance of a subject, even if the subject has taken long naps and the total amount of sleep time over the course of each day is relatively normal. For example, a person requiring eight hours of sleep may have only slept six hours each night over a three day period, but took a two hour nap each day. The total number of hours of sleep for each day equals the eight hours required by the person, but the person may not have experienced sufficient time in one or more particular sleep stages, resulting in sleep deprivation. Sleep deprivation can effect cognitive performance as well as the physical dexterity of the subject, and the point in a sleep cycle in which the subject has experienced just prior to waking can crucially affect the post-sleep dexterity, cognitive performance, and subjective feeling of the subject. For example, a sleeper wakened from late NREM stages 2 or 3 often experiences significant sleep inertia, a feeling of grogginess that may persist for up to thirty minutes after waking.

A large number of people have difficulties with falling asleep, maintaining sleep, experience frequent awakenings, or just do not use their sleep time as well as they could. The effects of even small amounts of sleep loss accumulate over time resulting in a "sleep debt" which manifests in increasing impairment of alertness, memory and decision-making Vigilance, memory, decision-making, and other neurocognitive processes are all impacted by poor sleep quality, sleep deprivation, and accumulating sleep debt with potentially detrimental consequences. For an example, recent National Aeronautics and Space Administration (NASA) technical reports reveal that pilots often experience brief episodes of unintentional sleep while flying. In the general population, chronic sleep loss is increasingly considered a serious public health and safety concern, and impaired vigilance is shown to be a primary contributor to transportation and industrial accidents.

To overcome sleep-related problems, some people take sleep inducing or assisting drugs, attend psychological therapy, try relaxing techniques prior to sleeping, or just deal with not sleeping well. Many other people do not realize they are not sleeping well and are, nonetheless, suffering the consequences of inefficient sleep.

SUMMARY

Systems and methods for optimizing the sleep performance of a subject person are provided. The systems and methods can be used to optimize the sleep and post-sleep performance of individuals regardless of their environment and time available for sleep. The systems and method may be used in domiciliary settings, such as in a subject's home and/or in operational settings, such as a hospital, sleep clinic, or a field deployment for industry or military. The systems and methods take into account factors that determine the effects of a sleep episode on dexterity, cognitive functions and the subjective feeling of fatigue after sleeping including duration and sleep architecture of the sleep episode, point on the circadian cycle at which the episode occurred, the amount of sleep debt accumulated prior to the episode and the subject's susceptibility to sleep deprivation. Embodiments of the systems and methods for obtaining efficient sleep periods also include monitoring of sleep architecture over a longer period of time (a couple of days, or a few weeks), measurement of accumulated sleep debt and assessment and/or tailoring of the sleep architecture for each subsequent sleep episode, determining a desired sleep state in which the subject should be in, and generating sensory stimuli for guiding the subject to the desired sleep state.

According to an embodiment, a method for optimizing the sleep of a subject is provided. The method includes monitoring at least one physiological characteristic of a subject indicative of a sleep state, and determining a current sleep state of the subject from the at least one monitored physiological characteristic. The method further includes determining a desired sleep state for the subject, and generating at least one sensory stimulus to guide the subject toward the desired sleep state if the current sleep state differs from the current sleep state.

According to another embodiment, an apparatus for optimizing sleep of a subject is provided. The apparatus includes a physiological characteristics monitor configured to monitor at least one physiological characteristic of a subject indicative of a sleep state of the subject and to generate physiological data representing the physiological characteristics of the subject. The apparatus also includes a data processor for processing the physiological data. The data processor includes a sleep staging component and a rules engine. The sleep staging component is configured to determine a current sleep state of the sleeper using the physiological data. The rules engine is configured to determine a desired sleep state for the subject and for determining one more stimuli to guide the subject to the desired sleep state from the current sleep state. The apparatus also includes a stimulus generator configured to generate the one or more stimuli to guide the subject toward the desired sleep state.

According to yet another embodiment, a computer-readable medium comprising processor-executable instructions that, when executed, direct a computer system to perform actions is provided. The computer-readable medium includes instructions for monitoring at least one physiological characteristic of a subject indicative of a sleep state, determining a current sleep state of the subject from the at least one monitored physiological characteristic, determining a desired sleep state for the subject, and generating at least one sensory stimulus to guide the subject toward the desired sleep state if the current sleep state differs from the current sleep state.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Embodiments of the present invention provide systems and method for optimization of sleep and post-sleep performance in operational and domiciliary settings by guiding a sleeper through an optimal sleep pattern with the goals of decreasing sleep latency, increasing sleep efficiency, ensuring balance among sleep states over longer periods of time and avoiding sleep inertia upon awakening. Embodiments of the present invention monitor physiological signals to identify a current sleep state being experienced by a sleeping subject, determine a desired sleep state that the subject should be experiencing based on sleep architecture data for the subject, identify sensory stimuli that may be applied to the subject to guide the subject to the desired sleep state from the current sleep state, and generate the sensory stimuli to guide the subject from the current sleep state to the desired sleep state. Continual monitoring of physiological signals of the sleeping subject allows the system to adapt to changes in the sleep state of the subject and to adjust the stimuli being generated. The sleeping subject may be guided through one or more intermediate sleep states in order to reach the desired sleep state. Embodiments also provide for detection and protection of the sleeping subject from environmental disturbances, such as noise, light, and temperature changes.

Embodiments also maintain a record of sleeping and napping episodes and the subject's sleep architecture over time (e.g. days, weeks, months). The cumulative sleeping and napping data can be used to develop a personalized sleep profile for the subject. The personalized sleep profile data can be used to generate a set of customized rules for determining an ideal sleep state for the subject based on the current sleep state of the subject and the parameters of the current sleep episode. The rules can be used to optimize a sleep episode and post-sleep performance. Post-sleep performance refers to the performance of a subject engaging in a task that requires use of motor and/or cognitive skills of the performer.

Embodiments of the present invention provide systems and methods for guiding the sleep of a subject to achieve efficient sleep periods of a subject even where there is little sleep time available, when the sleep periods are interrupted, or when the subject wishes to wake up a particular time. The systems and method can be used to optimize the sleep cycles of a subject to allow the subject to experience more efficient sleep, to wake feeling more refreshed, to require less sleep than the subject may have required without the optimizations, and to reduce the impact of sleep inertia.

Figure 1:
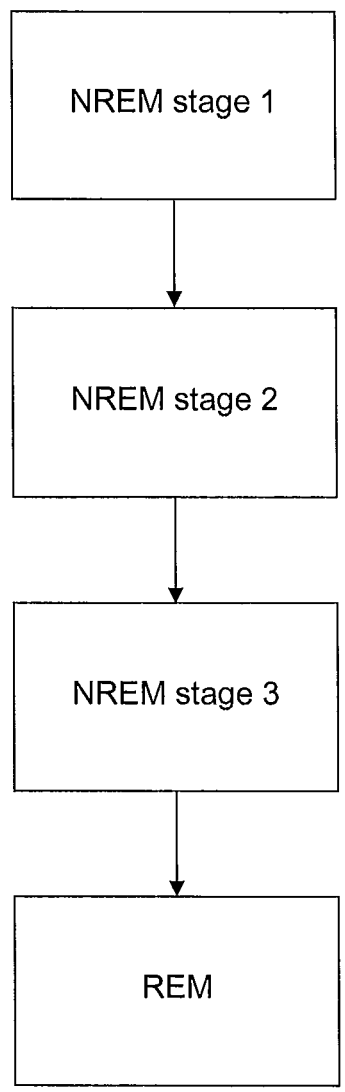
FIG. 1 is a block diagram illustrating a typical a sleep cycle.
Figure 2:
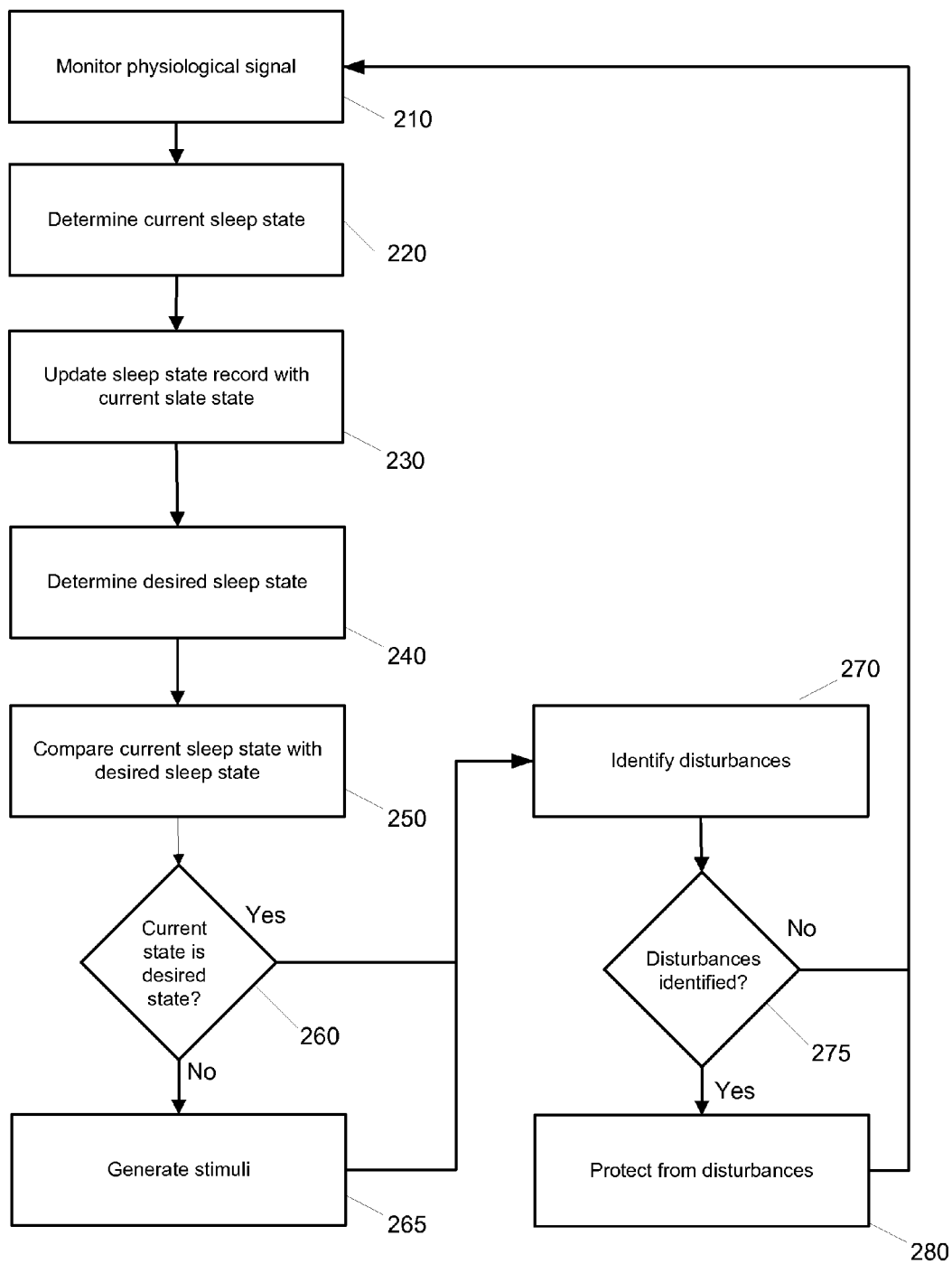
FIG. 2 is a flow diagram of a method for optimizing the sleep of a subject by guiding the subject to desired sleep stages according to an embodiment.

FIG. 2 is a flow diagram of a method for optimizing the sleep of a subject by guiding the subject through desired sleep stages according to an embodiment. Embodiments of the system which implements the described method are described afterwards. One or more physiological signals indicative of a sleep state of a sleeping subject are monitored (step 210). According to an embodiment, the physiological signals can include, but are not limited to, electroencephalogram (EEG), electrooculogram (EOG), electromyogram (EMG), respiration, heart rate, body movement, galvanic skin reaction, blood pressure, blood flow, blood chemistry, behavioral responses, or some combination thereof. In general, the signals are selected so as to provide information sufficient to identify sleep states and changes between them. Appropriate sensors and equipment for monitoring each of these physiological characteristics are well known in the art and are available from a variety of manufacturers.

A current sleep state of the subject is determined using the physiological signals (step 220). A As described above, conventional sleep science distinguishes between five different stages of sleep: a rested wakeful stage, NREM stages 1, 2, and 3, and the REM stage. Each of these stages may be distinguished from one another by reading various physiological signals of the subject. According to an embodiment, the physiological signals may be processed using a set of basic signal conditioning algorithms (e.g., artifact recognition and rejection, band-pass filtering, and/or other signal conditioning algorithms). According to an embodiment, the sleep state of the subject may be determined using well-known pattern recognition techniques to match the physiological signals obtained from the subject with one of the sleep stages described above.

The current sleep state information for the subject is then added to a sleep state record associated with the subject (step 230). According to an embodiment, the sleep state record associated with the user is stored in a relational database or other persistent data store. The sleep state record for the user also includes a record of recent sleep information representing the sleep architecture of several most recent sleep episodes of the subject. The sleep architecture associated with the subject is updated with the current sleep state for the subject at the end of each ongoing sleep episode.

A desired sleep state is then determined by applying a set of rules to the current sleep information and the recent sleep information (step 240). The rules aid in optimizing the sleep performance of the subject by identifying a desired sleep state that the subject should be experiencing at a particular time. A set of rules may be defined for a particular subject and/or a particular set of sleeping parameters. For example, a parasomiac subject—a person who experiences abnormal and unnatural movements, behaviors, emotions, perceptions, and/or dreams during certain stages or sleep and/or during transitions between certain stages of sleep—may have a specific set of rules defined for that subject that limit the time that the subject remains in certain stages of sleep. In another example, a set of rules may be defined for a subject who is on a military deployment or working shift work, where irregular and abbreviated periods of sleep can occur. According to some embodiments, the rules may be defined as a set of IF-THEN rules. For example, if the subject has not slept for more than thirty minutes with at least twenty minutes of NREM stage 2 sleep and the subject has not entered NREM stage 3 sleep, then the desired stage sleep state is the current sleep state. According to some embodiments, the rules may be developed through initial monitoring of sleep patterns and/or the physiological characteristics of a subject and/or by providing various sensory stimuli to the subject during sleep to determine the subject's physiological and sleep pattern responses to those sensory stimuli during sleep. According to an embodiment, the personalization of the rules to suit the needs of the particular sleeper can include
evaluating which physiological characteristics most clearly indicate a change between the sleeper's sleep states, which patterns of physiological characteristics occur at which portions of the sleeper's sleep cycle or under which circumstances, how a sleeper's physiological characteristics or sleep patterns change when exposed to sensory stimuli, how a sleeper's physiological characteristics respond when sleep is disrupted, optimal durations and patterns for a sleeper's sleep cycle, what sensory stimuli works most effectively to move the sleeper through the sleep stages, and/or other processes for calibrating the rules to the needs of a particular subject.

After the desired sleep state is determined using the rules, the desired sleep state is compared to the current sleep state for the subject (step 250), and a determination is made whether the current sleep state differs from the desired sleep state (step 260). If the current sleep state differs from the desired sleep state, sensory stimuli are generated to guide the sleep pattern of the subject toward the desired sleep state (step 265). The sensory stimuli can be any stimuli that can be sensed by a sleeping subject. According to some embodiments, sensory stimuli may include light, sound, smell, vibration, heat or cold, moisture, electric shock, and/or other stimuli that can be sensed by a sleeper. According to an embodiment, adjustments can be made to the sensory stimuli to lead the sleeping subject toward another sleep stage. These changes can include adjustments in the magnitude or quantity, tone, quality, pattern, frequency, application location or any other adjustment to sensory stimuli. Even minute changes to sensory stimuli may be sufficient to lead the sleeping subject toward another sleep stage. The type, duration, intensity and timing of generated stimuli depend on the current and desired sleep state and on whether a direct transition is physiologically possible or the sleeper needs to be led through some intermediate sleep state(s) prior to reaching the desired state. For an example, if the sleeper is awake while the desired state is NREM stage 2 sleep, soothing sounds may be generated to induce a transition from wakefulness through NREM stage 1 sleep to NREM stage 2. If for an example the sleeper is in NREM stage 3 sleep while the desired state is NREM stage 2 sleep, a combination of subliminal sounds and stroboscopic light flashes may be optimal. Continued monitoring of the physiological attributes of the subject can be used to determine whether the intended transition from one stage to sleep to another has taken place.

According to some embodiments, if the current sleep state does not differ from the desired sleep state, then no stimuli are generated to guide the sleep pattern of the subject because the subject is already in an optimal sleep stage. According to other embodiments, if the current sleep state of the subject matches the desired sleep state, one or more stimuli may be generated to help maintain the current sleep state of the subject.

Disturbances that may interrupt or negatively impact the sleep state of the subject are identified (step 270), and a determination is made whether any disruptive disturbances are present (step 275). Disturbances may include loud noise, strong light, temperature of the sleeping environment, and/or other potential distracters that may cause the subject to wake up frequently or prematurely or may prevent the subject from spontaneously entering into deeper stages of sleep are identified. If disruptive disturbances are present, the subject is protected from the disturbances by taking remedial actions. For example, if too much ambient light is present in the environment, the lights in the sleeping environment can be dimmed or the blinds closed to block sunlight or other light from outdoors from entering the room, or an eye mask or set of tinted glasses may be provided to block ambient light from reaching the subject's eyes. If the temperature of the room is too hot or too cold, a heating and ventilation system for the sleeping environment can be adjusted to adjust the temperature of the room to a more optimal sleeping temperature. If too much noise is present, a set of noise canceling headphones or earplugs may be provided, or white noise may be generated to block out the noise. If no disturbances are identified or the subject has been protected from the disturbances, the method returns to the monitoring step (step 210).

Figure 3:
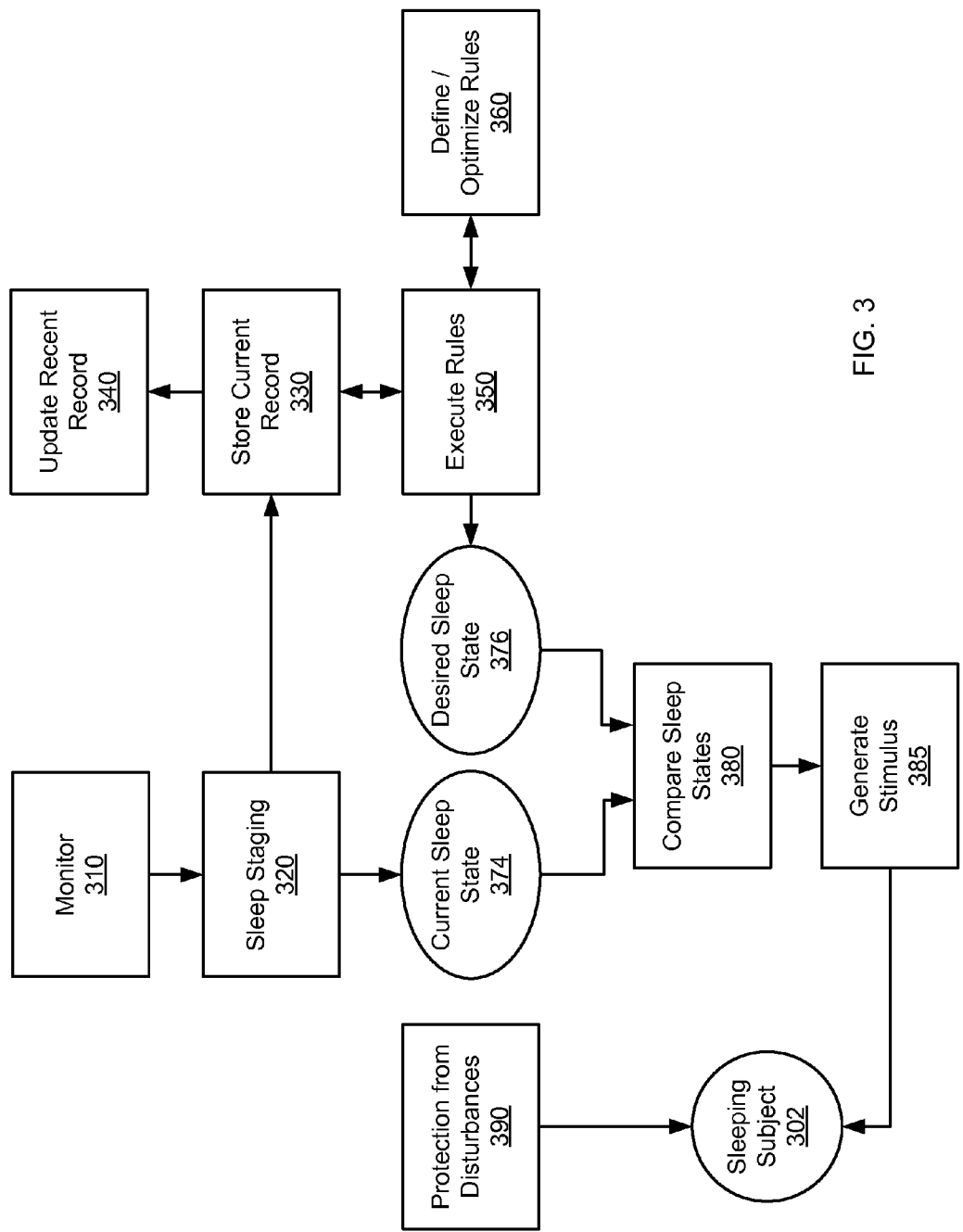
FIG. 3 is a block diagram illustrating the logical components of a sleep guidance system according to an embodiment.

FIG. 3 is a block diagram that illustrates the interaction of various functional components of a sleep guidance system according to an embodiment. In one embodiment, this system carries out the method described in connection with FIG. 2. Monitor module 310 monitors one or more physiological signals indicative of sleep state of the sleeping subject 302 (similar to step 210 of FIG. 2). As described above, various signals can be monitored, such as but not limited to, electroencephalogram (EEG), electrooculogram (EOG), electromyogram (EMG), respiration, heart rate, body movement, galvanic skin reaction, blood pressure, blood flow, blood chemistry, behavioral responses, or some combination thereof. The monitor module 310 receives signals from various sensors and/or monitoring equipment (not shown). Such sensors and/or monitoring equipment are well known in the art. Therefore detailed descriptions of these sensors and/or monitoring equipment have been omitted. The monitor component 310 outputs physiological data received from the various sensors and/or monitoring equipment, and this physiological data is input into sleep staging component 320.

According to an embodiment, sleep staging component 320 implements basic signal conditioning algorithms for cleaning up the physiological data received from the monitoring component 310. For example, artifact recognition and rejection, band-pass filtering, and other conditioning algorithms may be executed on the physiological data by the sleep staging component 320. The sleep stating component 320 also implements pattern recognition techniques for identifying patterns in the physiological data that can be used to detect a current sleep state of the subject 302 (similar to step 220 of FIG. 2). As described above, a subject typically exhibits specific physiological attributes during each stage of sleep that can be used to determine the current state of sleep that the subject is experiencing. Sleep staging component 320 outputs the current sleep state data 374 derived from the physiological data received from the monitoring component 320. The current sleep state data 374 represents a current stage of sleep that the sleeping subject 302 is experiencing.

The current sleep state is also provided to store current record component 330, which writes the current sleep data 374 to a sleep data store, such as a persistent memory (similar to step 230 of FIG. 2). According to an embodiment, the persistent data store may be implemented as a relational database that associates the current sleep data 374 with the subject. The information in the sleep data store can be later used to derive various descriptors of the sleep episode that can be, but are not limited to, total sleep time, time spent in each sleep state, percentage of each sleep state, position along a sleep cycle, and/or other information.

At the end of each sleep episode (when the subject 302 wakes), the update recent record component 340 updates the information about the sleep architecture of the several most recent sleep episodes of the subject (similar to step 230 of FIG. 2). This sleep architecture information is stored in the sleep data store.

Execute rules module 350 executes a set of rules on the information in the sleep data store including the data output from the store current record component 330 and the update recent record 340 to determine a desired sleep state that the subject should be experiencing in order to optimize the sleeping experience (similar to step 240 of FIG. 2). As described above, the rules that are executed may be customized for different subjects and/or sleeping situations or environments. The execute rules module 350 outputs desired sleep state data 374 that represents a desired sleep state that the sleeping subject 302 should be experiencing according to the rules.

Compare sleep states module 380 compares the current sleep state data 374 with the desired sleep state data 376 (similar to step 250 of FIG. 2), and if the current sleep state of the sleeping subject 302 differs from the desired sleep state, the compare sleep states module 380 identifies a set of stimuli that may be generated and applied to the subject 302 in order to guide the sleeping subject 302 from the current sleep state to the desired sleep state. The subject 302 may need to be guided through one or more intermediary sleep states in order to reach the desired sleep state.

The generate stimulus module 385 receives control signals from the compare sleep states module 380 that indicates the pattern of sensory stimuli the generate stimulus module 385 should generate in order to guide the subject 302 to the desired sleep state (similar to step 265 of FIG. 2). According to some embodiments, the generate stimulus module 385 may also be instructed to generate sensory stimuli either at selected intervals or continuously throughout a sleep period so that the subject 302 reaches a sleep stage near an awake stage of the sleep cycle within a predetermined period of time at the end of the sleep period. For example, if the subject 302 needs to awaken at 6:00 am, the generate stimulus module 385 may generate stimuli to guide the subject 302 toward reaching an awake state between 5:45 am and 6:00 am. By guiding the subject 302 toward an awake state prior to waking the subject 302, the subject may wake more refreshed and with lesser impact from sleep inertia. According to some embodiments, the generate stimulus module 385 may also be instructed to generate at least one sensory stimulus to cause the sleeper to remain in the current sleep state; and wherein the stimulus generator is configured to generate the at least one sensory stimulus to cause the sleeper to remain in the current sleep state. For example, if the subject 302 has already reached NREM stage 3 and NREM stage 3 is the desired sleep stage for the subject 302, the generate stimulus module 385 may generate stimuli that encourage the subject 302 to remain in NREM stage 3.

The define and optimize rules module 360 provides an interface that enables the rules to be executed by execute rules module 350 to be defined, modified, and/or deleted. According to an embodiment, the define and optimize rules module 360 provides a graphical user interface, such as a web page or executable application, that enables a user to define new rules and modify or delete existing rules. According to an embodiment, the define and optimize rules module provides an interface for receiving input for creating and/or modifying rules from computer systems and/or various instruments for monitoring the physiological attribute of the subject 302.

According to an embodiment, protection from disturbances module 390 identifies potential distracters in the operational environment, such as loud noise, strong light, high or low temperatures, that may cause the subject to wake prematurely or may prevent the subject from spontaneously entering into deeper stages of sleep (similar to step 270 of FIG. 2). Automatic and/or manual steps may be taken to attenuate or block potential distracter (similar to step 280 of FIG. 2). The protection from disturbances module 390 can automatically takes steps to attenuate or block the potential distracters, such as dimming lights, adjusting the temperature of a heating and cooling system, performing active noise cancellation, and/or other steps to block or attenuate potential distracters. According to some embodiments, manual steps may also be taken to attenuate or block the potential distracters, such as placing a mask or dark glasses on the subject to block light, provide earplugs or headphones to the subject to block and/or attenuate noise. According to some embodiments, the protection from disturbances module 390 may alert either the subject or an attendant (depending upon the operational environment) to take one or more manual steps to attenuate or block the potential distracters.

Figure 4:
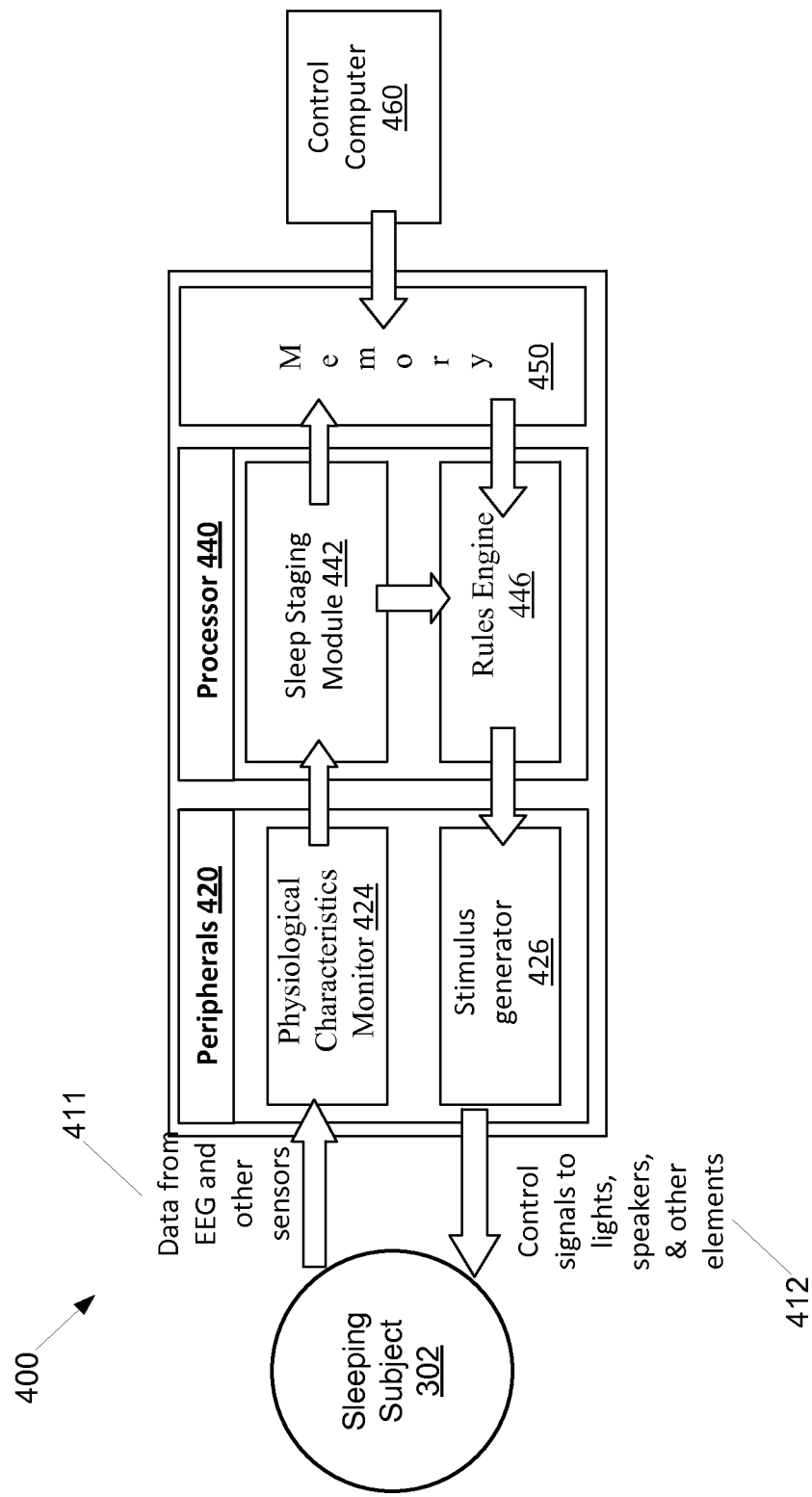
FIG. 4 is a high level block diagram of a sleep guidance system according to an embodiment.

FIG. 4 illustrates an exemplary sleep guidance system 400 according to an embodiment. Sleep guidance system 400 includes a data processor 440. System 400 is an example of one possible configuration of software and/or hardware that may be used to implement the method illustrated in FIG. 2 and the functional components of a sleep guidance system illustrated in FIG. 3. According to an embodiment, data processor 440 comprises a computer system that includes one or more microprocessors for executing instructions, such as a personal computer system, laptop computer, or server. Data processor 440 controls the operation of the sleep guidance system 400 to guide a subject 302 through one or more sleep cycles. The data processor 440 is configured, through hardware, software or both, to communicate with each of a number of associated peripherals 420.

Data processor 440 includes a sleep staging module 442 and rules engine 446. Sleep staging module 442 receives physiological data output by physiological characteristics monitor 424.

According to an embodiment, sleep staging module 442 implements basic signal conditioning algorithms for cleaning up the physiological data received from the physiological characteristics monitor 424. For example, artifact recognition and rejection, band-pass filtering, and other conditioning algorithms may be executed on the physiological data by the sleep staging module 442. The sleep staging module 442 also implements pattern recognition techniques for identifying patterns in the physiological data that can be used to detect a current sleep state of the subject 302.

Rules engine 446 executes rules, such as those described above with respect to step 250 of FIG. 2, to determine a desired sleep stage for the subject which can then be used to determine the types of stimulus that the simulus generator 426 of peripherals 420 should generate.

Simulus generator 426 can generate various control signals 412 that control various peripherals that apply various stimuli to subject 302, such as those described above with respect to step 265 of FIG. 2. For example, the stimulus generator 426 may generate control signals that control lights, speakers, and/or other devices that generate stimuli such as light, sound, and changes in temperature.

Data processor 440 may be configured differently for each embodiment of the invention to enable the various sleep guidance rules and to coordinate monitoring of physiological signals, interpreting of the physiological data received, mapping the sleep patterns and physiological signals of the sleeper throughout the sleep cycle, determining of a sleeper's current sleep state, identifying of which physiological characteristics indicate when a sleeper is about to transition to a new sleep state and which sensory stimuli characteristics will guide the sleeper to transition to a new sleep state, and generating of sensory stimuli to guide the sleeper to the new sleep state.

Sleep guidance system 400 includes one or more peripherals 420 operatively coupled to data processor 440 to provide various stimuli for guiding the sleep of the subject 302 and for monitoring various physiological characteristics of the subject 302. For example, physical characteristics monitor 424 can receive signals 411 from various sensors used to detect physiological characteristics of subject 302. According to some embodiments, the sensors include electroencephalographs, electrooculograms, electromyograms, microphones, motion sensors, moisture sensors, blood pressure cuffs, thermistors or nasal cannulas connected to a pressure transducer, pulse oximeters, thermometers or other temperature sensing device, and/or any other sensor that can detect a physiological characteristic of the subject 302.

Sleep guidance system 400 includes sensory stimulus generator 426 operatively coupled to data processor 440. The sensory stimulus generator 426 provides sensory stimuli to the sleeping subject 302. The sensory stimulus generator 426 includes at least one stimuli source devices used to generate stimuli that may be perceived by the sleeping subject 302 through the sleeping subject 110's senses. According to an embodiment, the stimuli source devices can include speakers, vibrators, lights, electric contacts, fans, heaters, coolers, and/or other devices that can generate stimuli that may be perceived through sleeping subject 110's senses. The stimulus generator 426 can include various components for providing sensory stimuli to the sleeping subject 302. According to an embodiment the components of the stimulus generator 426 can include ear phones, a mask that fits over the eyes and/or face of subject 302, a headband, a belt, a wristband, a ring, and/or other components that enable the stimulus source devices to convey stimuli to the subject 302.

Sleep guidance system 400 also includes memory 450. Memory 450 is a computer-readable memory, such as a read-only memory (ROM), random-access memory (RAM), a flash memory, magnetic media memory, and/or other memory for storing data to be used by and/or generated by sleep guidance system 400 and/or executable program code that may be executed by data processor 440.

According to some embodiments, a control computer system 460 is used to program data processor 440 of the sleep guidance system 400. Control computer system 460 can be used to define rules for determining desired sleep states and/or to personalize sleep profiles. Alternatively, that functionality can be implemented by the processor 440 coupled with appropriate user interface peripherals. Various types of computer systems may be used for control computer system 460, such as a personal computer system, a laptop computer system, a handheld computer system or the like. According to an embodiment, the sleep guidance system 400 provides a graphical user interface, such as a web page or executable application, that enables a user to define new rules and modify or delete existing rules. According to an embodiment, the sleep guidance system 400 provides an interface for receiving input for creating and/or modifying rules from computer systems and/or various instruments for monitoring the physiological attribute of the subject 302.

One embodiment of the sleep guidance system 400 is for use in operational environments, such as in shift work environments where workers are working shifts that disrupt typical sleep patterns or on military field deployments where personnel in the field may experience extended periods of disrupted sleep patterns. The signals 411 used for monitoring and determining the sleeper's sleep states comprise EEG recorded from the forehead using dry electrodes, two modified EOG channels (left and right epicanthus referenced to nasion) and head movements recorded with an accelerometer. According to an embodiment, the stimulus generator 426 includes thick, yet soft ear covers that provide attenuation of environmental noise, and embedded ear pads with small speakers to deliver audio stimulation to the subject 302. According to an embodiment, a thick and soft eye mask or a set of non-transparent glasses serve to block out environmental light. According to some embodiments, the eye mask or glasses house one or more light emitting elements that provide visual stimulation, and according to some embodiments, the eye mask or the glasses include one or more heating and/or cooling elements. The rules used by rules engine 446 for determining desired sleep states are configured to balance the sleep cycle of the subject 302 to create a balance between NREM stage 2, NREMS stage 3, and REM sleep over long periods of time, such as a couple of days, and to gradually wake up the subject 302 when required so as to avoid significant sleep inertia that can impair the post-sleep performance of the subject 302. One aspect of this embodiment is on portability, light weight, simplicity and providing protection from environmental disturbances.

Another embodiment of the sleep guidance system 400 is for use in the treatment of parasomnias secondary to a psychiatric condition. In this embodiment, the rules used by rules engine 446 used to drive the stimulus generator 426 are defined create stimuli that cause the sleeping subject 302 to not enter sleep states in which nightmares, bed wetting, or sleepwalking can occur.

FIG. 4 merely illustrates one possible configuration of a sleep guidance system. Different combinations of elements can be used to adapt the sleep guidance system to various environments, such as hospitals, homes, businesses, and field deployments. According to some embodiments, the attenuation of environmental disturbances is not required, because the sleeping subject is expected to use the sleep guidance system in the subject's home or in a hospital room where environmental disturbances are less likely.

Those of skill in the art will appreciate that the various illustrative modules, components, engines, and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules, components, engines, and method steps described in connection with the embodiments disclosed herein can be implemented or performed with hardware such as a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor is hardware and can be a microprocessor, but in the alternative, the processor can be any hardware processor or controller, microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm and the functionality of a component, engine, or module described in connection with the embodiments disclosed herein can be embodied directly in hardware, in software executed by a processor, or in a combination of the two. Software can reside in computer or controller accessible computer-readable storage media including RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

What is claimed is:

1. A method for optimizing sleep of a subject, the method comprising:
monitoring at least one physiological characteristic of a subject indicative of a sleep state using signals recorded from the subject's forehead by one or more sensors;
using at least one hardware processor of a portable device configured to be worn by the subject,
determining a current sleep state of the subject from the at least one monitored physiological characteristic, wherein the current sleep state comprises one of rapid-eye-movement (REM) sleep, non-rapid-eye-movement (NREM) sleep stage one, NREM sleep stage two, and NREM sleep stage three, and
determining a desired sleep state for the subject based on one or more rules, the determined current sleep state, and a record of prior sleep states for the subject stored in a memory of the portable device, and wherein the one or more rules are configured to determine a desired sleep state that maintains a balance between REM sleep, NREM sleep stage one, NREM sleep stage two, and NREM sleep stage three and avoids sleep inertia;
if the desired sleep state is different than the current sleep state, generating, using at least an eye mask comprising one or more light-emitting elements and one or more heating elements, at least one sensory stimulus to guide the subject toward the desired sleep state; and,
if the desired sleep state is the same as the current sleep state, generating, using at least the one or more heating elements of the eye mask, at least one sensory stimulus to cause the subject to remain in the current sleep state.

2. The method of claim 1, further comprising:
maintaining a sleep architecture record that includes current and previous sleep episode information for the subject;
wherein determining a desired sleep state for the subject comprises executing the one or more rules on the sleep architecture record for the subject to determine the desired sleep state for the subject.

3. The method of claim 1, further comprising:
attenuating at least one environmental disturbance.

4. The method of claim 3, wherein attenuating at least one environment disturbance includes at least one of performing passive noise attenuation, performing active noise cancellation, and performing passive attenuation of light.

5. The method of claim 1, wherein the at least one sensory stimulus for guiding the subject toward the desired sleep state includes performing at least one of: decreasing sleep latency, increasing sleep efficiency, shortening the duration of a sleep cycle, and preventing sleep inertia upon awakening.

6. The method of claim 1 wherein monitoring at least one physiological characteristic of the subject comprises monitoring at least one of: brain waves, eye movements, muscle tone, respiration, heart rate, blood pressure, body temperature, blood flow, blood oxygen level, blood chemistry, galvanic skin reaction, moisture, body position, and body motion.

7. The method of claim 1, wherein the at least one sensory stimulus comprises a thermal stimulus which comprises heating or cooling at least one area of skin of the subject.

8. The method of claim 1, further comprising:
indicating a sleep period duration for monitoring the at least one physiological characteristic; and
generating sensory stimuli at selected intervals throughout the sleep period duration to guide the subject through sleep stages so that the subject reaches a sleep stage near an awake stage of sleep during a predetermined time period at an end of the sleep period.

9. The method of claim 1, further comprising obtaining a measure of accumulated sleep debt.

10. The method of claim 1, wherein the eye mask further comprises one or more speakers configured to deliver audio stimulation.

11. An apparatus for optimizing sleep of a subject, the apparatus comprising a standalone portable device configured to be worn by the subject, wherein the standalone portable device comprises:
a memory;
a physiological characteristics monitor that monitors at least one physiological characteristic of a subject indicative of a sleep state of the subject using signals recorded from the subject's forehead by one or more sensors, and generates physiological data representing the at least one physiological characteristic of the subject;
a data processor that determines a current sleep state of the subject using the physiological data, wherein the current sleep state comprises one of rapid-eye-movement (REM) sleep, non-rapid-eye-movement (NREM) sleep stage one, NREM sleep stage two, and NREM sleep stage three, and determines a desired sleep state for the subject based on one or more rules, the determined current sleep state, and a record of prior sleep states for the subject stored in the memory, and wherein the one or more rules are configured to determine a desired sleep state that maintains a balance between REM sleep, NREM sleep stage one, NREM sleep stage two, and NREM sleep stage three and avoids sleep inertia; and
a stimulus generator that, if the desired sleep state is different than the current sleep state, generates, using at least an eye mask comprising one or more light-emitting elements and one or more heating elements, one or more stimuli to guide the subject toward the desired sleep state, and, if the desired sleep state is the same as the current sleep state, generates, using at least the one or more heating elements of the eye mask, at least one or more stimuli to cause the subject to remain in the current sleep state.

12. The apparatus of claim 11, further comprising
an environmental disturbance attenuation component configured to identify and attenuate or eliminate at least one environmental disturbance.

13. The apparatus of claim 12, wherein the environmental disturbance attenuation component performs at least one of:
passive noise attenuation;
active noise cancellation;
passive light attenuation.

14. The apparatus of claim 11 wherein the physiological characteristic monitor is configured to monitor at least one of the following physiological characteristics of the subject: brain waves, eye movements, muscle tone, respiration, heart rate, blood pressure, body temperature, blood flow, blood oxygen level, blood chemistry, galvanic skin reaction, body position, and body motion.

15. The apparatus of claim 11 wherein the stimulus generator is configured to generate at least one of an audible sound, a visible light, a thermal stimulus, a scent, a touch, a vibration, and an electric shock.

16. The apparatus of claim 11 wherein the stimulus generator is configured to generate a thermal stimulus which includes heating or cooling at least one area of skin of the subject.

17. The apparatus of claim 11 wherein the data processor further:
receives feedback through the physiological characteristic monitor indicating whether the subject is moving toward or maintaining a desired sleep state; and
adjusts one or more characteristics of the one or more stimuli generated by the stimulus generator to further cause the subject to change to or remain in the desired sleep stage.

18. The apparatus of claim 11, wherein the data processor further:
receives an input indicating a sleep period duration for monitoring the physiological characteristic; and
generates one or more stimuli throughout the sleep period duration at selected intervals to guide the subject through a sequence of sleep states so that the subject is in a sleep stage near an awake state around an end of the sleep period duration.

19. The apparatus of claim 18, wherein the data processor further generates sensory stimuli continuously throughout the sleep period duration to lead the subject through sleep.

20. The apparatus of claim 19, wherein the data processor further stores information about sleep architecture of current and previous episodes of sleep in the memory.

21. The apparatus of claim 18, wherein the data processor stores information about the current sleep state in the memory upon determining the current sleep state.

22. The apparatus of claim 11 wherein the standalone portable device is configured to be coupled to a control computer system comprising control software for programming the standalone portable device, the control computer system being used to define thresholds and the one or more rules for determining a desired sleep state of the subject.

23. The apparatus of claim 22, wherein the standalone portable device is configured to be coupled to the control computer system over the Internet, enabling the standalone portable device to be configured remotely using the control computer system.

24. The apparatus of claim 22, wherein the standalone portable device is configured to be coupled to the control computer system using at least one of a wired connection and a wireless connection.

25. The apparatus of claim 11, wherein the data processor further obtains a measure of accumulated sleep debt.

26. The apparatus of claim 11, wherein the eye mask further comprises one or more speakers configured to deliver audio stimulation.

* * * * *